(12) United States Patent
Plata-Salaman et al.

(10) Patent No.: US 6,627,653 B2
(45) Date of Patent: Sep. 30, 2003

(54) ANTICONVULSANT DERIVATIVES USEFUL FOR THE TREATMENT OF DEPRESSION

(75) Inventors: Carlos R. Plata-Salaman, Ambler, PA (US); Josue Bacaltchuk, Sao Paulo (BR); Pedro A. S. Prado-Lima, Alegre (BR)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/916,742

(22) Filed: Jul. 27, 2001

(65) Prior Publication Data

US 2002/0094960 A1 Jul. 18, 2002

Related U.S. Application Data

(60) Provisional application No. 60/222,489, filed on Aug. 2, 2000.

(51) Int. Cl.[7] .................. A61K 31/35; A61K 31/355; A61K 31/18
(52) U.S. Cl. .................. 514/454; 514/455; 514/456; 514/459; 514/601
(58) Field of Search ................................. 514/454, 455, 514/456, 459, 601

(56) References Cited

U.S. PATENT DOCUMENTS

| | | | |
|---|---|---|---|
| 3,621,096 A | * | 4/1969 | prange et al. ............ 424/244 |
| 4,513,006 A | | 4/1985 | Maryanoff et al. |
| 5,242,942 A | | 9/1993 | Costanzo et al. |
| 5,387,700 A | | 2/1995 | Maryanoff et al. |
| 5,753,693 A | | 5/1998 | Shank |
| 6,322,503 B1 | * | 11/2001 | Sparhawk, Jr. ........... 600/300 |

FOREIGN PATENT DOCUMENTS

| | | |
|---|---|---|
| WO | WO 9800123 A | 1/1998 |
| WO | WO 99/62522 A1 | 12/1999 |
| WO | PCT/US01/23786 | 7/2001 |

OTHER PUBLICATIONS

"Conventional and New Antidepressant Drugs in the Elderly", Gareri et al., Progress in Neurobiology 61, 2000, 353–396.*

Topiramate in Treatment–Refractory Depression; Pedro A.S. Prado–Lima et al original poster presentation Aug. 1999.

Prado–Lima, Topiramate in Treatment–Resistant Depression, letter to editor, not accepted for publication e–mail regarding chat room/bulletin board posting.

Dursun S M et al: "Accelerated weight loss after treating refractory depression with fluoxetine plus topiramate: possible mechanisms of action?." Canadian Journal of Psychiatry. Revue Canadienne de Psychiatrie, (Apr. 2001) 46 (3) 287–8. XPO01029971 The Whole Document.

Data Base Adislerts 'Online! Prado Lima Pa S et al: "Topiramate in treatment–refractory depression" retrieved from STN Database accession No. 1999:61852 XP002179442 abstract & 11th World Congress of Psychiatry (Aug. 6, 1999), vol. 2, 00. 126.

Garonna F et al: "Topiramate in the treatment of over–weight/obese binge eaters ADIS Title: Topiramate: therapeutic use. ; Obesity; In patient with binge eating disorders" International Journal of Neuropsychopharmacology Int J Neuropsychopharmacol 3(Suppl 1): 299 Jul. 2000. (Jul. 1, 200), XP001030426 Bassano dG, Vicenza, Italy the whole document.

Database ADISalerts 'Online! McElroy S L et al: "A pilot trial of adjunctive topiramate in the treatment of bipolar disorder ADIS Title: Topiramate: therapeutic use.; Bipolar disorder: A pilot trial of adjunctive treatment" retrieved from STN Database accession No. 1998:39968 XP002179443 abstract & XXIST CINP Congress (Jul. 12, 1998), PP 281 (Poster), University of Cincinnati College of Medicine, Cincinatti, Ohio, USA.

Databse Drugnl 'Online! "Topiramate" retrieved from STN Database accession No. 1998:2562 XP002179444 abstract & R&D Focus Drug News, Jul. 27, 1998.

Sanacora G. et al: "Impairment of GABAergic transmission in depression: New insights from neuroimaging studies." Critical Reviews in Neurobiology, (2000) 14/1 (23–45)., xp001029967 the whole document.

Kuziecky R et al: "Topiramate Increase Cerebral GABA in Healthy Humans" Neurology, Lippincott Williams $ Wilkins, Philadelphia, US, No. 51, Aug. 1998, pp. 627–629, XP000923467 ISSN:0028–3878 the whole document.

Kyowa Hakko: "Topiramate" Drugs of the Future, Barcelona, ES, vol. 21, No. 4, 1996, pp. 463–465, XP002043895 ISSN 0377–8282 the whole document.

Langtry H.D. et al: "Topiramate, A review of its pharmacodynamic and pharmacokinetic properties and clinical efficacy in the management of epilepsy." Drugs, (1997) 54/5 (752–773)., xp002179441 the whole document.

Robert M. Berman, et al, "Treatment–Refranctoy Depression: Definitions and Characteristics", Depression and Anxiety, 1997, 154–164,5.

* cited by examiner

Primary Examiner—Zohreh Fay
Assistant Examiner—Brian-Yong S. Kwon
(74) Attorney, Agent, or Firm—Ralph R. Palo

(57) ABSTRACT

Anticonvulsant derivatives useful for treating depression as monotherapy or combination therapy are disclosed.

8 Claims, No Drawings

ANTICONVULSANT DERIVATIVES USEFUL FOR THE TREATMENT OF DEPRESSION

CROSS REFERENCE TO RELATED APPLICATIONS

This application claims priority from U.S. provisional application Ser. No. 60/222,489 file Aug. 02, 2000, the contents of which are hereby incorporated by reference.

BACKGROUND OF THE INVENTION

The present invention is directed to anticonvulsant derivatives useful in the treatment of depression, specifically unipolar depression, treatment-refractory depression, resistant depression, anxious depression and dysthymia. The present invention is further directed to the treatment of depression comprising administration of one or more anticonvulsant derivatives in combination with one or more compounds selected from mono-amine oxidase inhibitors, tricyclics, serotonin reuptake inhibitors, serotonin noradrenergic reuptake inhibitors, noradrenergic and specific serotonergic agents, noradrenaline reuptake inhibitors, natural products, dietary supplements, neuropeptides, compounds targeting neuropeptide receptors or hormones.

Compounds of Formula I:

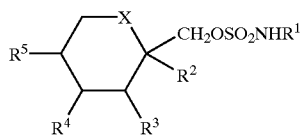

(I)

are structurally novel antiepileptic compounds that are highly effective anticonvulsants in animal tests (MARYANOFF, B. E, NORTEY, S. O., GARDOCKI, J. F., SHANK, R. P. AND DODGSON, S. P. *J. Med. Chem.* 1987, 30, 880–887; MARYANOFF, B. E., COSTANZO, M. J., SHANK, R. P., SCHUPSKY, J. J., ORTEGON, M. E., AND VAUGHT J. L. *Bioorg. Med. Chem. Lett.* 1993, 3, 2653–2656; SHANK, R. P., GARDOCKI, J. F., VAUGHT, J. L., DAVIS, C. B., SCHUPSKY, J. J., RAFFA, R. B., DODGSON, S. J., NORTEY, S. O., MARYANOFF, B. E. Epilepsia 1994, 35, 450–460; MARYANOFF B E, COSTANZO M J, NORTEY S O, GRECO M N, SHANK R P, SCHUPSKY J J, ORTEGON M P, VAUGHT J L. *J. Med. Chem.* 1998, 41, 1315–1343). These compounds are covered by three U.S. Pat. Nos.: 4,513,006, 5,242,942, and 5,384,327. One of these compounds 2,3:4,5-bis-O-(1-methylethylidene)-β-D-fructopyranose sulfamate, known as topiramate, has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., *Epilepsia* 1995, 36 (S4), 33; S. K. SACHDEO, R. C. SACHDEO, R. A. REIFE, P. LIM and G. PLEDGER, *Epilepsia* 1995, 36 (S4), 33; T. A. GLAUSER, *Epilepsia* 1999, 40 (S5), S71–80; R. C. SACHDEO, Clin. Pharmacokinet. 1998, 34, 335–346), and is currently marketed for the treatment of seizures in patients with simple and complex partial epilepsy and seizures in patients with primary or secondary generalized seizures in the United States, Europe and most other markets throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., *Epilepsia* 1994, 35, 450–460). Subsequent studies revealed that Compounds of Formula I were also highly effective in the MES test in rats. Topiramate was also found to effectively block seizures in several rodent models of epilepsy (J. NAKAMURA, S. TAMURA, T. KANDA, A. ISHII, K. ISHIHARA, T. SERIKAWA, J. YAMADA, and M. SASA, *Eur. J. Pharmacol.* 1994, 254, 83–89), and in an animal model of kindled epilepsy (A. WAUQUIER and S. ZHOU, *Epilepsy Res.* 1996, 24, 73–77).

Compounds of formula I have further been found to be effective in the treatment of manic depressive bipolar disorder (Shank, U.S. Pat. No. 5,753,693).

Tollefson et al in WIPO Publication WO99/62522 disclose a method for the treatment of bipolar disease, bipolar depression or unipolar depression comprising administration of an atypical antipsychotic in combination with a compound selected from the group consisting of serotonin reuptake inhibitors, anticonvulsants and lithium.

Unipolar depression is defined as depressed mood on a daily basis for a minimum duration of two weeks. An episode may be characterized by sadness, indifference or apathy, or irritability and is usually associated with a change in a number of neurovegetative functions, including sleep patterns, appetite and body weight, motor agitation or retardation, fatigue, impairment in concentration and decision making, feelings of shame or guilt, and thoughts of death or dying (*Harrison's Principles of Internal Medicine*, 2000). The criteria for a major depressive episode includes five or more symptoms present during the same 2-week period, where this represents a change from previous functioning; and where at least one of the symptoms is either depressed mood or loss of interest or pleasure. Symptoms of a depressive episode include depressed mood; markedly diminished interest or pleasure in all, or almost all, activities most of the day; weight loss when not dieting or weight gain, or decrease or increase in appetite nearly every day; insomnia or hypersomnia nearly every day; psychomotor agitation or retardation nearly every day; fatigue or loss of energy nearly every day; feelings of worthlessness or excessive or inappropriate guilt nearly every day; diminished ability to think or concentrate, or indecisiveness, nearly every day; recurrent thoughts of death, recurrent suicidal ideation without a specific plan, or a suicide attempt or a specific plan for committing suicide. Further, the symptoms cause clinically significant distress or impairment in social, occupational, or other important areas of functioning. (*Diagnostic and Statistical Manual of Mental Disorders*, 4th Edition, American Psychiatric Association, 1994).

Current treatment options for unipolar depression include monotherapy or combination therapy with various classes of drugs including mono-amine oxidase inhibitors, tricyclics, serotonin reuptake inhibitors, serotonin noradrenergic reuptake inhibitors, noradrenergic and specific serotonergic agents, noradrenaline reuptake inhibitor, "natural products" (such as Kava-Kava, St. John's Wort), dietary supplement (such as s-adenosylmethionine) and others. More specifically, drugs used in the treatment of depression include, but are not limited to imipramine, amitriptyline, desipramine, nortriptyline, doxepin, protriptyline, trimipramine, maprotiline, amoxapine, trazodone, bupropion, chlomipramine, fluoxetine, citalopram, sertraline, paroxetine, fluvoxamine, nefazadone, venlafaxine, reboxetine, mirtazapine, phenelzine, tranylcypromine, and/or moclobemide (eg, J. M. KENT, Lancet 2000, 355, 911–918; J. W. WILLIAMS JR, C. D. MULROW, E. CHIQUETTE, P. H. NOEL, C. AGUILAR, and J. CORNELL, *Ann. Intern. Med.* 2000, 132, 743–756; P. J. AMBROSINI, *Psychiatr. Serv.* 2000, 51, 627–633). Several of these agents including, but not limited to, serotonin reuptake inhibitors are also used when depression and anxiety co-exist, such as in anxious depression (R. B. LYDIARD and O. BRAWMAN-MINTZER, *J. Clin. Psychiatry* 1998, 59, Suppl. 18, 10–17; F. ROUILLON, *Eur. Neuropsychopharmacol.* 1999, 9 Suppl. 3, S87–S92).

In the clinic, 40–50% of depressed patients who are initially prescribed antidepressant therapy do not experience a timely remission of depression symptoms. This group typifies treatment-refractory depression, that is, a failure to demonstrate an "adequate" response to an "adequate" treatment trial (that is, sufficient intensity of treatment for sufficient duration) (R. M. BERMAN, M. NARASIMHAN, and D. S. CHARNEY, *Depress. Anxiety* 1997, 5, 154–164). Moreover, about 20–30% of depressed patients remain partially or totally resistant to pharmacological treatment including combination treatments (J. ANANTH, *Psychother. Psychosom.* 1998, 67, 61–70; R. J. CADIEUX, *Am. Fam. Physician* 1998, 58, 2059–2062). Increasingly, treatment of resistant depression includes augmentation strategies including treatment with pharmacological agents such as, lithium, carbamazepine, and triiodothyronine, and the like (M. HATZINGER and E. HOLSBOER-TRACHSLER, *Wien. Med. Wochenschr.* 1999, 149, 511–514; C. B. NEMEROFF, *Depress. Anxiety* 1996–1997, 4, 169–181; T. A. KETTER, R. M. POST, P. I. PAREKH and K. WORTHINGTON, *J. Clin. Psychiatry* 1995, 56, 471–475; R. T. JOFFE, W. SINGER, A. J. LEVITT, C. MACDONALD, *Arch. Gen. Psychiatry* 1993, 50, 397–393).

Dysthymia is defined as a mood disorder characterized by chronic depressed mood for a period of at least 2 years. Dysthymia can have a persistent or intermittent course and the depressed mood occurs for most of the day, for more days than not, and for at least 2 years. (*Diagnostic and Statistical Manual of Mental Disorders,* 4$^{th}$ Edition, American Psychiatric Association, 1994).

Bipolar disorder, on the other hand, is characterized by unpredictable swings in mood between mania and depression (bipolar I disorder) or between hypomania and depression (bipolar II disorder) (*Diagnostic and Statistical Manual of Mental Disorders,* 4$^{th}$ Edition, American Psychiatric Association, 1994). Antidepressant use in bipolar disorder is generally, intentionally restricted to avoid the risk of mania and the risk of rapid cycling induced by antidepressants in bipolar disorder (H. J. MOLLER and H. GRUNZE, *Eur. Arch. Psychiatry Clin. Neurosci.* 2000, 250, 57–68; J. R. CALABRESE, D. J. RAPPORT, S. E. KIMMEL, and M. D. SHELTON, *Eur. Neuropsychopharmacol.* 1999, 9, S109–S112). Moreover, none of the mood stabilizers used in bipolar disorder have proven antidepressive efficacy (H. J. MOLLER and H. GRUNZE, *Eur. Arch. Psychiatry Clin. Neurosci.* 2000, 250, 57–68).

DISCLOSURE OF THE INVENTION

Accordingly, it has been found that compounds of the following formula (I):

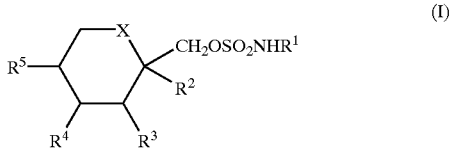

wherein X is O or $CH_2$, and $R^1$, $R^2$, $R^3$, $R^4$ and $R^5$ are as defined hereinafter are useful in treating depression, specifically unipolar depression, treatment-refractory depression, resistant depression, anxious depression and dysthymia.

In an embodiment of the present invention, the depression is selected from the group consisting of unipolar depression, treatment refractory depression, resistant depression and anxious depression.

In an embodiment of the present invention is a method for the treatment of depression comprising administering to a subject in need thereof a combination of one or more compounds of formula I with one or more compounds selected from the group consisting of mono-amine oxidase inhibitors such as phenelzine, tranylcypromine, moclobemide, and the like; tricyclics such as imipramine, amitriptyline, desipramine, nortriptyline, doxepin, protriptyline, trimipramine, chlomipramine, amoxapine, and the like; tetracyclics such as maprotiline, and the like; non-cyclics such as nomifensine, and the like; triazolopyridines such as trazodone, and the like; serotonin reuptake inhibitors such as fluoxetine, sertraline, paroxetine, citalopram, fluvoxamine, and the like; serotonin receptor antagonists such as nefazadone, and the like; serotonin noradrenergic reuptake inhibitors such as venlafaxine, milnacipran and the like; noradrenergic and specific serotonergic agents such as mirtazapine, and the like; noradrenaline reuptake inhibitors such as reboxetine, and the like; atypical antidepressants such as bupropion, and the like; natural products such as Kava-Kava, St. John's Wort, and the like; dietary supplements such as s-adenosylmethionine., and the like; and neuropeptides such as thyrotropin-releasing hormone and the like, and the like; compounds targeting neuropeptide receptors such as neurokinin receptor antagonists and the like; and hormones such as triiodothyronine, and the like.

In an embodiment of the present invention is a method for the treatment of depression comprising administering to a subject in need thereof a combination of one or more compounds of formula I with one or more compounds selected from the group consisting of mono-amine oxidase inhibitors; tricyclics; tetracyclics; non-cyclics; triazolopyridines; serotonin reuptake inhibitors; serotonin receptor antagonists; serotonin noradrenergic reuptake inhibitors; serotonin noradrenergic reuptake inhibitors; noradrenergic and specific serotonergic agents; noradrenaline reuptake inhibitors; atypical antidepressants; natural products; dietary supplements; neuropeptides; compounds targeting neuropeptide receptors; and hormones.

Preferably, one or more compounds of formula I are administered in combination with one or more compounds selected from the group consisting of mono-amine oxidase inhibitors, tricyclics, serotonin reuptake inhibitors, serotonin noradrenergic reuptake inhibitors; noradrenergic and specific serotonergic agents and atypical antidepressants.

More preferably, one or more compounds of formula I are administered in combination with one or more compounds selected from the group consisting of mono-amino oxidase inhibitors, tricyclics and serotonin reuptake inhibitors.

Most preferably, one or more compounds of formula I are administered in combination with one or more compounds selected from the group consisting of serotonin reuptake inhibitors.

In an embodiment of the present invention is a method for the treatment of depression comprising administering to a subject in need thereof a combination of one or more compounds of formula I with one or more compounds selected from the group consisting of phenelzine, tranylcypromine, moclobemide, imipramine, amitriptyline, desipramine, nortriptyline, doxepin, protriptyline, trimipramine, chlomipramine, amoxapine, fluoxetine, sertraline, paroxetine, citalopram, fluvoxamine, venlafaxine, milnacipran, mirtazapine, bupropion, thyrotropin-releasing hormone and triiodothyronine.

Preferably, one or more compounds of formula I are administered in combination with one or more compounds selected from the group consisting of phenelzine, tranylcypromine, moclobemide, imipramine, amitriptyline, desipramine, nortriptyline, doxepin, protriptyline, trimipramine, chlomipramine, amoxapine, fluoxetine, sertraline, paroxetine, citalopram, fluvoxamine, venlafaxine, milnacipran, mirtazapine and bupropion.

More preferably, one or more compounds of formula I are administered in combination with one or more compounds selected from the group consisting of phenelzine, tranylcypromine, moclobemide, imipramine, amitriptyline, desipramine, nortiptyline, doxepin, protriptyline, trimipramine, chlomipramine, amoxapine, fluoxetine, sertraline, paroxetine, citalopram and fluvoxamine.

Most preferably, one or more compounds of formula I are administered in combination with one or more compounds selected from the group consisting of fluoxetine, sertraline, paroxetine, citalopram and fluvoxamine.

In an embodiment of the present invention, is a method for the treatment of depression comprising administering to a subject in need thereof a combination of one or more compounds of formula I with one or more compounds selected from the group consisting of neuropeptides such as thyrotropin-releasing hormone and the like; compounds targeting neuropeptide receptors such as neurokinin receptors antagonists and the like; and hormones such as triiodothyronine and the like.

DETAILED DESCRIPTION OF THE PREFERRED EMBODIMENTS

As used herein, the term "depression" shall be defined as unipolar depression, treatment-refractory depression, resistant depression, anxious depression and dysthymia.

The sulfamates of the invention are of the following formula (I):

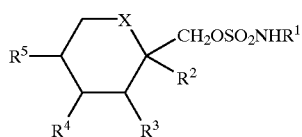

(I)

wherein
X is $CH_2$ or oxygen;
$R^1$ is hydrogen or alkyl; and $R^2$, $R^3$, $R^4$ and $R^5$ are independently hydrogen or lower alkyl and, when X is $CH_2$, $R^4$ and $R^5$ may be alkene groups joined to form a benzene ring and, when X is oxygen, $R^2$ and $R^3$ and/or $R^4$ and $R^5$ together may be a methylenedioxy group of the following formula (II):

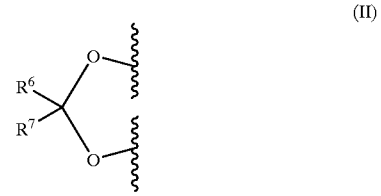

(II)

wherein
$R^6$ and $R^7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R^2$, $R^3$, $R^4$, $R^5$, $R^6$ and $R^7$ are of about 1 to 3 carbons and include methyl, ethyl, iso-propyl and n-propyl. When X is $CH_2$, $R^4$ and $R^5$ may combine to form a benzene ring fused to the 6-membered X-containing ring, i.e., $R^4$ and $R^5$ are defined by the alkatrienyl group =C—CH=CH—CH=.

A particular group of compounds of formula (I) is that wherein X is oxygen and both $R^2$ and $R^3$ and $R^4$ and $R^5$ together are methylenedioxy groups of the formula (II), wherein $R^6$ and $R^7$ are both hydrogen both alkyl or combine to form a spiro cyclopentyl or cyclohexyl ring, in particular where $R^6$ and $R^7$ are both alkyl such as methyl. A second group of compounds is that wherein X is $CH_2$ and $R^4$ and $R^5$ are joined to form a benzene ring. A third group of compounds of formula (I) is that wherein both $R^2$ and $R^3$ are hydrogen.

The compounds of formula (I) may be synthesized by the following methods:

(a) Reaction of an alcohol of the formula $RCH_2OH$ with a chlorosulfamate of the formula $ClSO_2NH_2$ or $ClSO_2NHR^1$ in the presence of a base such as potassium t-butoxide or sodium hydride at a temperature of about −20° to 25° C. and in a solvent such as toluene, THF, or dimethylformamide wherein R is a moiety of the following formula (III):

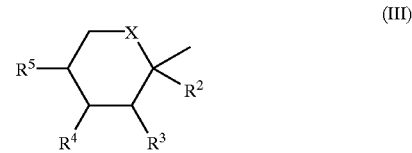

(III)

(b) Reaction of an alcohol of the formula $RCH_2OH$ with sulfurylchloride of the formula $SO_2Cl_2$ in the presence of a base such as triethylamine or pyridine at a temperature of about −40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R^1NH^2$ at a temperature of abut 40° to 25° C. in a solvent such as methylene chloride or acetonitrile to produce a compound of formula (I). The reaction conditions for (b) are also described by T. Tsuchiya et al. in *Tetrahedron Lett.*, 1978, 3365.

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah in *Tetrahedron Lett.* 1975, 2455. The azidosulfate is then reduced to a compound of formula (I) wherein $R^1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R^2$ and $R^3$ and $R^4$ and $R^5$ are identical and are of the formula (II) may be obtained by the method of R. F. Brady in *Carbohydr. Res.* 1970, 14, 35 or by reaction of the trimethylsilyl enol ether of a $R^6COR^7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al. in *J. Org. Chem.* 1973, 38, 3935.

Further, carboxylic acids and aldehydes of the formulae RCOOH and RCHO may be reduced to compounds of the formula $RCH_2OH$ by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in "Modern Synthetic Reactions", 2nd Ed., pages 45 to 144 (1972).

The compounds of formula I: may also be made by the process disclosed U.S. Pat. Nos.: 4,513,006, 5,242,942, and 5,384,327, which are incorporated by reference herein.

The compounds of formula I include the various individual isomers as well as the racemates thereof, e.g., the various alpha and beta attachments, i.e., below and above the plane of the drawing, of $R^2$, $R^3$, $R^4$ and $R^5$ on the 6-membered ring. Preferably, the oxygen of the methylenedioxy group (II) are attached on the same side of the 6-membered ring.

The ability of the compounds of formula I to treat depression is based on the results of clinical case studies in which topiramate was added to existing pharmacotherapy in two patients with diagnosed depression.

EXAMPLE 1

In the first case, the patient was a female who had suffered from depression for 25 years. In addition, the patient exhibited anxiety, sensitivity to her environment, and presented with a history of migraine headaches, obesity and two suicide attempts.

Previous pharmacological treatment history included unsuccessful treatment of patient's depression with the combination of clomipramine+lithium+carbamazepine and only partial response with the combinations of imipramine+ fluoxetine+carbamazepine and venlafaxine+mirtazapine.

Topiramate was prescribed for the patient as add-on therapy to existing treatment of venlafaxine at 225 mg/day and mirtazapine at 30 mg/day. Topiramate treatment was initiated at 25 mg/day, with increased dosage to 150 mg/day. After two months, with topiramate dosage at 150 mg/day, the patient was reevaluated as "very mild depressive". After six months, mirtazapine was withdrawn and topiramate daily dosage increased to 200 mg/day. At this point, the patient was evaluated as "very much improved". Topiramate dosage was further increased to 300 mg/day and after eight months patient's depression was "very much improved".

Following one year, topiramate and venlafaxine were withdrawn because of a surgical procedure. The patient experienced relapse in depression, binge eating symptoms and body weight gain. The patient was subsequently restarted on topiramate at 300 mg/day. Following six months of treatment, the patient reported "feeling very well", had reduced anxiety and depression, with increased initiative and confidence.

EXAMPLE 2

In the second case, the patient was a female who had suffered from depression, binge eating and obesity for 11 years. In addition, the patient exhibited anxiety, aggression and sensitivity to her environment. She had no history of mania or hypomania and no relatives with bipolar disorder.

Previous pharmacological treatment history included unsuccessful treatment of patient's depression with amitriptyline, tranylcypromine and the combination therapies of fluoxetine+nortriptyline+triiodothyronine and paroxetine+carbamazepine+amphepramone.

The patient's depression appeared controlled with a combination of 300 mg/day venlafaxine, 800 mg/day carbamazepine, 40 mg/day methylphenidate and 2 mg/day risperidone. However, the patient experienced mild relapses of depression over a period of about two years.

Initially the patient was started on topiramate add-on therapy at 25 mg/day, with increased dosage to 150 mg/day over the course of one month, in response to the patient's clinical behavior (the patient experienced suicidal ideation). One month later, the topiramate therapy was further increased to 300 mg/day, with the patient also taking 20 mg/day methylphenidate and 150 mg/day venlafaxine. At this time the patient was rated "much improved", with resolved suicidal ideation. After three month of treatment, the patient reported that she had "never felt so well". She had clear thoughts, good concentration, better performance at work, and felt less tired. Her feelings of hostility and hypersensitivity to the environment had also resolved. At eight months of therapy, she continued to be normothymic and to feel very well. Compared with her state of well-being on commencing of treatment, she felt happier, had more pleasure and interests, was outgoing, energetic and creative, had better memory and concentration, normal libido, less irritability, and improved social and work performance. By this time the patient was only taking venlafaxine at 150 mg/day and topiramate at 300 mg/day.

Thus, for treating depression, a compound of formula I may be employed by administering repeated oral doses in the range of about 10 to 650 mg daily, more preferably in the range of about 16 to 325 mg once or twice daily. Further, for treating depression, the compound of formula I may used as monotherapy or as a component in combination therapy.

Optimal dosages to be administered may be readily determined by those skilled in the art, and will vary with the particular compound or compounds used, the mode of administration, the strength of the preparation and the advancement of the disease condition. In addition, factors associated with the particular patient being treated, including patient's sex, age, weight, diet, time of administration and concomitant diseases, will result in the need to adjust dosages.

As used herein, the term "subject" shall refer to an animal, preferably a mammal, most preferably a human, who is the object of treatment, observation or experiment.

As used herein, the term "therapeutically effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amount, as well as any product which results, directly or indirectly, from combinations of the specified ingredients in the specified amount.

To prepare the pharmaceutical compositions of this invention, one or more compounds of formula I are intimately admixed with a pharmaceutical carrier according to conventional pharmaceutical compounding techniques, which carrier may take a wide variety of forms depending on the form of preparation desired for administration, e.g., i.v. sterile injectable formulations will be prepared using appropriate solubilizing agents. A unit dose would contain about 15 to 200 mg of the active ingredient. Topiramate is currently available for oral administration in round tablets containing 25 mg, 100 mg or 200 mg of active agent. The tablets contain some or all of the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

Wherein the present invention is directed to pharmaceutical administration of one or more compounds of formula I, the compound(s) of formula I may be administered by any suitable method, as would be apparent to one skilled in the art. More particularly, the compound(s) of formula I may be administered by any parenteral method including, but not limited to oral pulmonary, intraperitoneal (ip), intravenous (iv), intramuscular (im), subcutaneous (sc), transdermal, buccal, nasal, sublingual, ocular, rectal and vaginal. The compounds(s) of formula I, including topiramate, may also be administered directly to the nervous system, including but not limited to, via intracerebral, intraventricular, intracerebroventricular, intrathecal, intracisternal, intraspinal and/or peri-spinal routes of administration by delivery via intracranial or intravertebral needles and/or catheters with or without pump devices. It will be readily apparent to those skilled in the art that any dose or frequency of administration that provides the therapeutic effect described herein is suitable for use in the present invention.

In certain embodiments of the present invention, the compound of formula I may be administered in combination with one or more compounds as previously described, preferably in combination with one to three compounds, more preferably in combination with one to two compounds.

Wherein the present invention is directed to the administration of a combination, the compounds may be co-administered simultaneously, sequentially, separately or in a single pharmaceutical composition. Where the compounds are administered separately, the number of dosages of each compound given per day, may not necessarily be the same, e.g. where one compound may have a greater duration of activity, and will therefore, be administered less frequently. Further, the compounds may be administered via the same or different routes of administration, and at the same or different times during the course of the therapy, concurrently in divided or single combination forms. The instant invention is therefore understood as embracing all regimens of simultaneous or alternating treatment and the term "administering" is to be interpreted accordingly.

Wherein the present invention is directed to therapy with a combination of agents, "therapeutically effective amount" shall mean that amount of the combination of agents taken together so that the combined effect elicits the desired biological or medicinal response. For example, the therapeutically effective amount of combination therapy comprising a compound of formula I and a serotonin reuptake inhibitor would be the amount of the compound of formula I and the amount of the serotonin reuptake inhibitor that when taken together or sequentially have a combined effect that is therapeutically effective, more preferably where the combined effect is synergistic. Further, it will be recognized by one skilled in the art that in the case of combination therapy with a therapeutically effect amount, the amount of each component of the combination individually may or may not be therapeutically effective.

Therapeutically effective dosage levels and dosage regimens for mono-amine oxidase inhibitors, tricyclics, serotonin reuptake inhibitors, serotonin noradrenergic reuptake inhibitors, noradrenergic and specific serotonergic agents, noradrenaline reuptake inhibitor, natural products, dietary supplements, neuropeptides, compounds targeting neuropeptide receptors, hormones and other pharmaceutical agents disclosed herein, may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http:/// www.pdrel.com) or other sources.

To prepare a pharmaceutical composition of the present invention wherein the compound of formula I is administered in combination with one or more compounds as previously described, the dosages of the individual compounds are selected in such a manner as to provide effective levels of each of the compounds in the body at the same time and may vary depending on the particular compound administered and general and specific responses to the compound. Further, the ratio of the compounds may be varied as to optimize therapeutic synergy. Wherein the compounds are administered in a single dosage form, the pharmaceutical composition may be prepared according to conventional pharmaceutical compounding techniques and may include intimately admixing the active compounds with one or more pharmaceutical carriers, excipients and/or additives.

While the foregoing specification teaches the principles of the present invention, with examples provided for the purpose of illustration, it will be understood that the practice of the invention encompasses all of the usual variation, adaptations and/or modifications as come within the scope of the following claims and their equivalents.

What is claimed is:

1. A method for treating depression in a subject afflicted with such condition comprising administering to the subject a therapeutically effective amount of a compound of the formula I

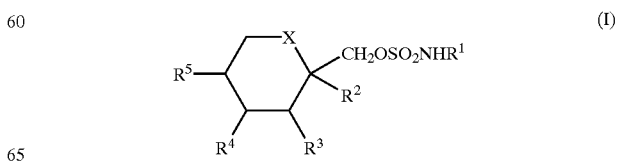

wherein
X is CH$_2$ or oxygen;
R$^1$ is hydrogen or alkyl; and
R$^2$, R$^3$, R$^4$ and R$^5$ are independently hydrogen or lower alkyl and, when X is CH$_2$, R$^4$ and R$^5$ may be alkene groups joined to form a benzene ring and, when X is oxygen, R$^2$ and R$^3$ and/or R$^4$ and R$^5$ together may be a methylenedioxy group of the following formula (II):

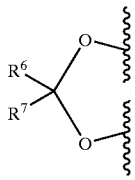
(II)

wherein
R$^6$ and R$^7$ are the same or different and are hydrogen, lower alkyl or are alkyl and are joined to form a cyclopentyl or cyclohexyl ring, alone or
in combination with one or more compounds selected from the group consisting of mono-amine oxidase inhibitors, tricyclics, serotonin reuptake inhibitors, serotonin noradrenergic reuptake inhibitors, noradrenergic and specific serotonergic agents, noradrenaline reuptake inhibitor, natural products, dietary supplements, neuropeptides, compounds targeting neuropeptide receptors and hormone, wherein said depression is selected from the group consisting of treatment-retractory depression, resistant depression, anxious depression and dysthymia.

2. The method of claim 1 wherein the compound of formula I is administered in combination with one or more compounds selected from the group consisting of imipramine, amitriptyline, desipramine, nortriptyline, doxepin, protriptyline, trimipramine, maprotiline, amoxapine, trazodone, bupropion, chlomipramine, fluoxetine, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, neurokinin receptor antagonists and triiodothyronine.

3. The method of claim 1, wherein the compound of formula I is topiramate.

4. The method of claim 1, wherein the therapeutically effective amount is from about 10 to 650 mg daily.

5. The method of claim 1, wherein the amount is from about 16 to 325 mg once or twice daily.

6. The method of claim 1, wherein the compound of formula I is topiramate and is administered in combination with one or more compounds selected from the group consisting of mono-amine oxidase inhibitors, tricyclics, serotonin reuptake inhibitors, serotonin noradrenergic reuptake inhibitor, noradrenergic and specific serotonergic agents and atypical antidepressants.

7. The method of claim 6 wherein the compound of formula I is topiramate and is administered in combination with one or more compounds selected from the group consisting of phenelzine, tranylcypromine, moclobemide, imipramine, amitriptyline, desipramine, nortriptyline, doxepin, protriptyline, trimipramine, chlomipramine, amoxapine, fluoxetine, sertraline, paroxetine, citalopram, fluvoxamine, venlafaxine, milnacipran, mirtazapine and bupropion.

8. The method of claim 1, wherein the compound of formula I is topiramate and is administered in combination with one or more compounds selected from the group consisting of neuropeptides, compounds targeting neuropeptide receptors and hormones.

* * * * *